(12) United States Patent
He

(10) Patent No.: US 6,569,162 B2
(45) Date of Patent: May 27, 2003

(54) PASSIVELY SELF-COOLED ELECTRODE DESIGN FOR ABLATION CATHETERS

(76) Inventor: Ding Sheng He, 377 Wesford Rd., Tyngsboro, MA (US) 01879-2418

( * ) Notice: Subject to any disclaimer, the term of this patent is extended or adjusted under 35 U.S.C. 154(b) by 0 days.

(21) Appl. No.: 09/821,490

(22) Filed: Mar. 29, 2001

(65) Prior Publication Data

US 2003/0028185 A1 Feb. 6, 2003

(51) Int. Cl.⁷ ............................................... A61B 18/14
(52) U.S. Cl. ........................... 606/41; 606/32; 606/48
(58) Field of Search ...................................... 606/32–52

(56) References Cited

U.S. PATENT DOCUMENTS

| | | |
|---|---|---|
| 3,911,928 A | 10/1975 | Legergren |
| 4,074,718 A | 2/1978 | Morrison, Jr. |
| 4,532,924 A | 8/1985 | Auth et al. |
| 4,649,937 A | 3/1987 | DeHaan et al. |
| 5,257,635 A | 11/1993 | Langberg |
| 5,334,193 A | 8/1994 | Nardella |
| 5,348,554 A | 9/1994 | Imran et al. |
| 5,423,811 A | 6/1995 | Imran et al. |
| 5,437,662 A | 8/1995 | Nardella |
| 5,462,521 A | 10/1995 | Brucker et al. |
| 5,545,161 A | 8/1996 | Imran |
| 5,697,927 A | 12/1997 | Imran et al. |
| 5,779,699 A * | 7/1998 | Lipson .......................... 606/41 |
| 5,836,875 A | 11/1998 | Webster, Jr. |
| 5,863,290 A | 1/1999 | Gough et al. |
| 6,071,278 A | 6/2000 | Panescu et al. |
| 6,077,257 A | 6/2000 | Edwards et al. |
| 6,178,354 B1 | 1/2001 | Gibson |
| 6,394,949 B1 * | 5/2002 | Crowley et al. ............ 600/104 |

\* cited by examiner

*Primary Examiner*—Roy D. Gibson
*Assistant Examiner*—Henry M. Johnson, III
(74) *Attorney, Agent, or Firm*—Kudirka & Jobse, LLP

(57) ABSTRACT

A self-cooling electrode for use with an ablation catheter has greater surface area that allows electrode to dissipate heat to the blood pool more effectively and increased thermal mass, and, therefor greater heating capacity/thermal conductivity for improved heat transfer between the electrode and tissue for more effective tissue heating. The electrode design allows increased power to be delivered with minimized risk of overheating or coagulation at the tissue-electrode interface. The increased thermal mass and thermal conductivity of the electrode design are achieved with a substantially solid electrode body with thick walls. Cooling and increased heat exchange are achieved with an alternating pattern of channels and projections that collectively define a plurality of edges either parallel or perpendicular to the electrode axis. Blood or other biological fluids can flow through the channels along the exterior surface of the electrode to help cool the electrode while heat is simultaneously transferred from the electrode body, edges and projections to the surrounding tissue. A catheter having a self cooled tip electrode, in conjunction with one or more ring electrodes, may be used to form a large virtual electrode capable of creating longer, deeper tissue lesions.

19 Claims, 8 Drawing Sheets

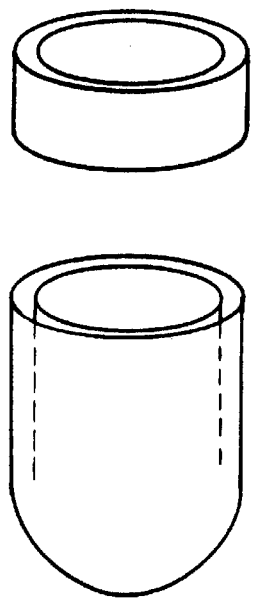
Figure 1 (PRIOR ART)
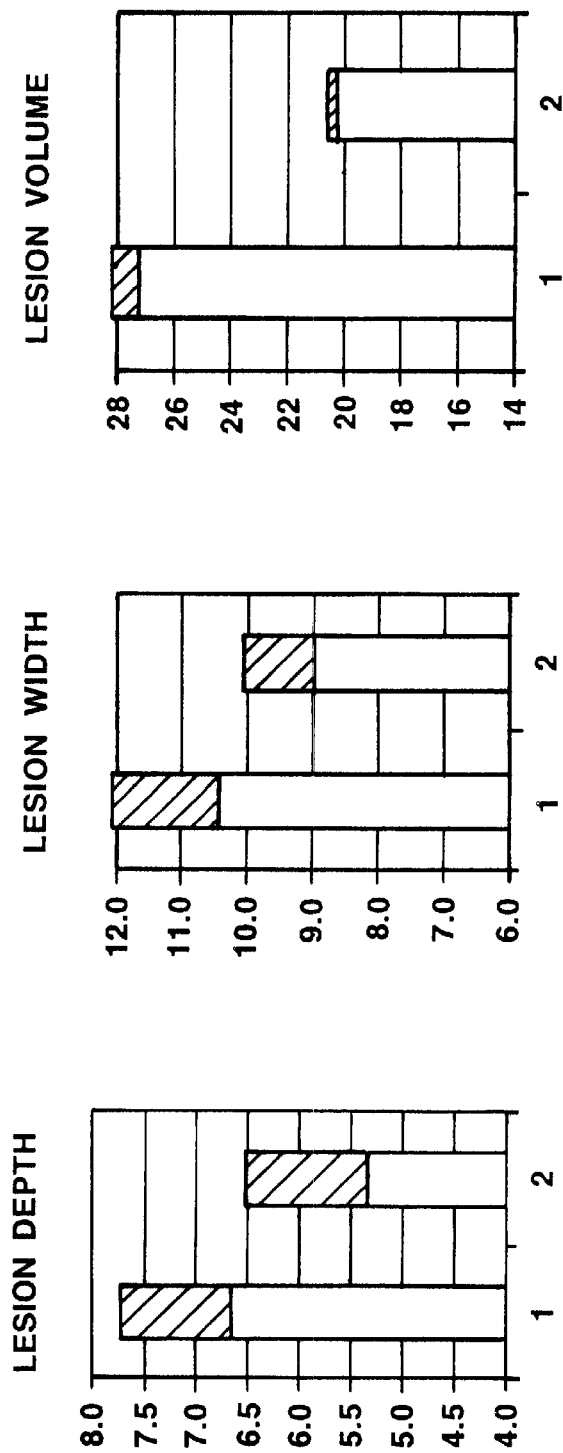
Figure 15
Figure 14
Figure 13

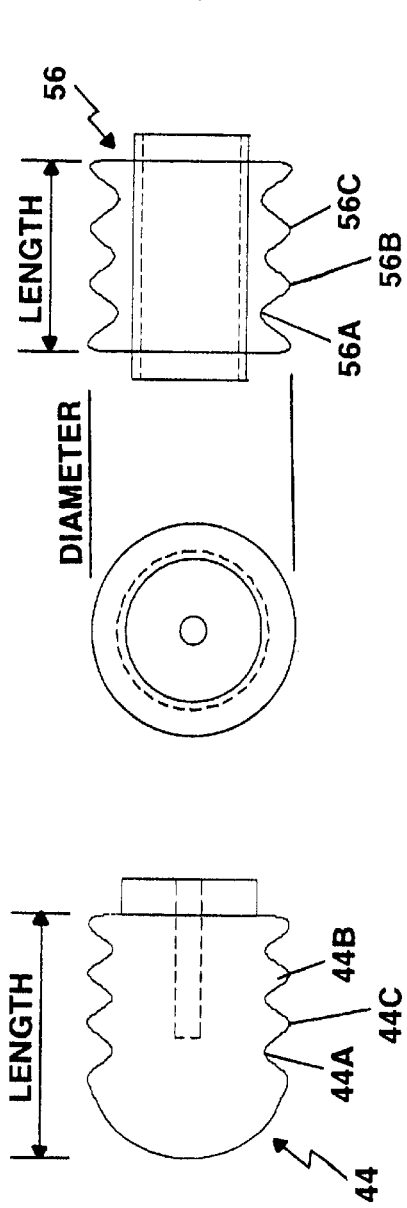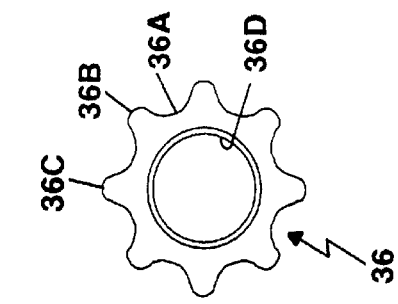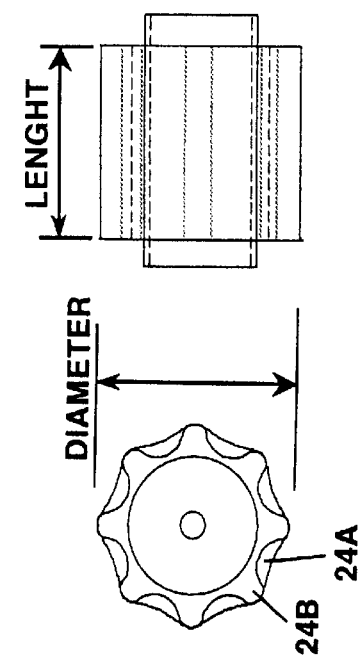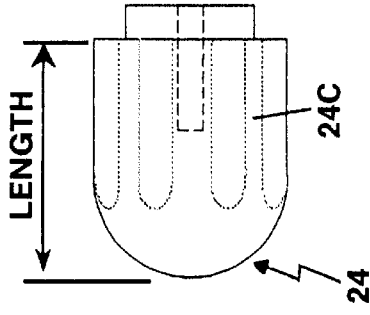

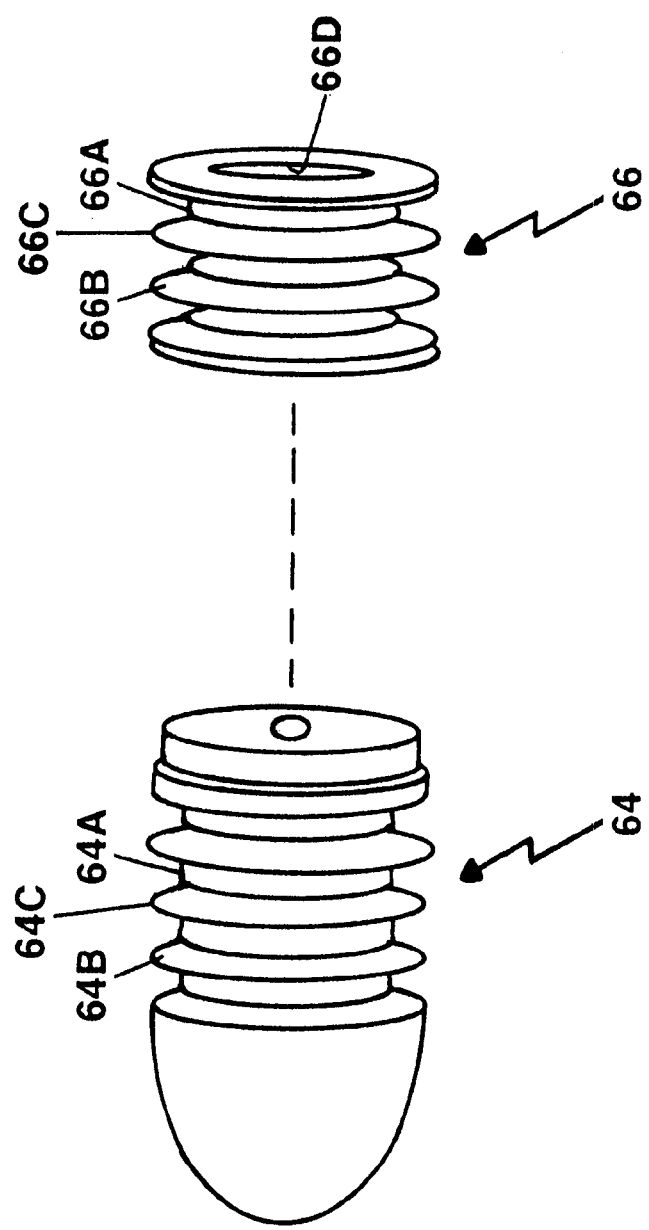

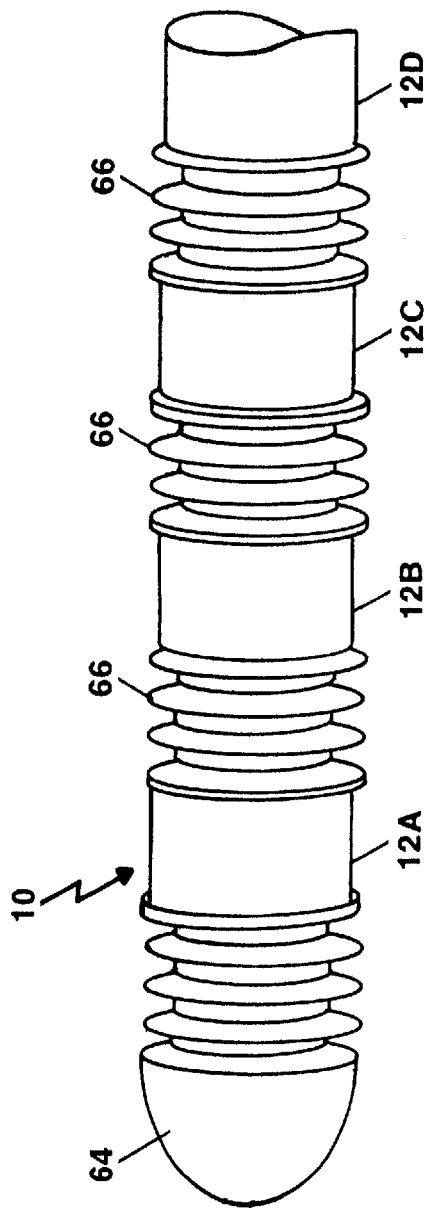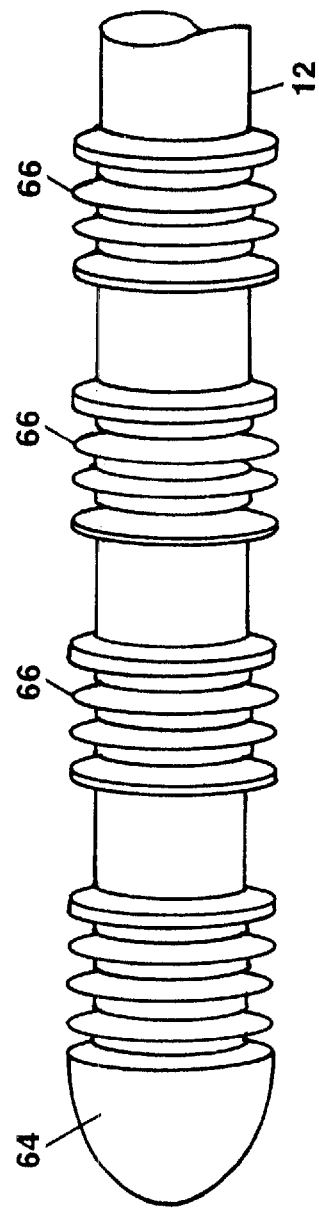
Figure 10A
Figure 10B

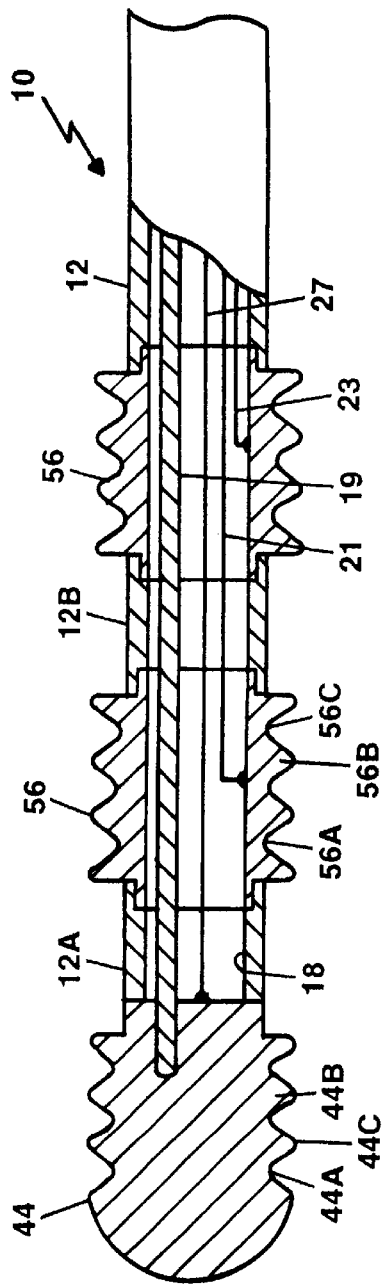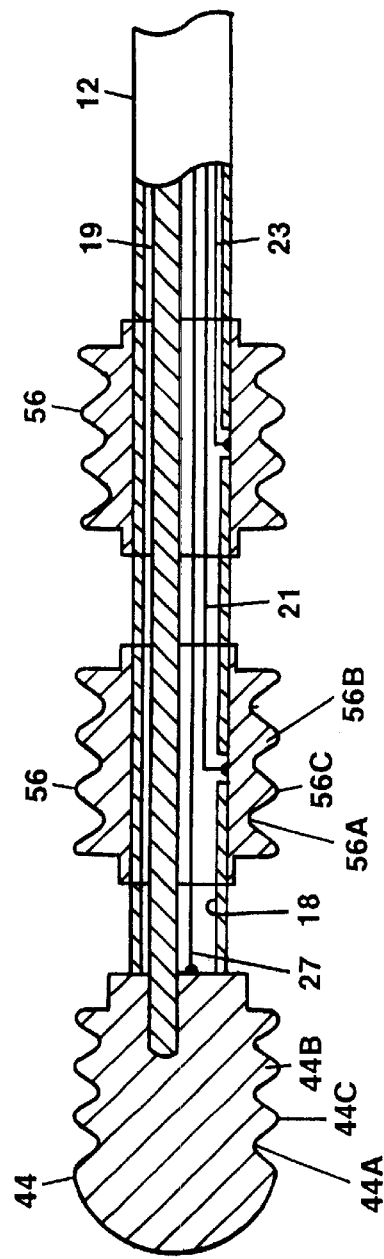
Figure 12A
Figure 12B

PASSIVELY SELF-COOLED ELECTRODE DESIGN FOR ABLATION CATHETERS

The application is related to and claims priority to U.S. Provisional patent application Ser. No. 60/193,199 filed Mar. 20, 2000, entitled SELF-COOLED ELECTRODE DESIGN FOR CATHETER ABLATION OF TISSUE ENABLES DEEPER LESIONS, the entirety of which is incorporated herein by reference.

FIELD OF THE INVENTION

This invention relates generally to ablation catheters and, more particularly, to a self-cooled electrode design for use with ablation catheters that results in more controlled heating and ablation of tissue.

BACKGROUND OF THE INVENTION

The pumping action of the heart is controlled in an orderly manner by electrical stimulation of myocardial tissue. Stimulation of this tissue in the various regions of the heart is controlled by a series of conduction pathways contained within the myocardial tissue. At the completion of ventricular stimulation, heart tissue rests to allow the cells to recover for the next stimulation. The stimulation is at the cellular level, and is a changing of the polarity of the cells from positive to negative.

Cardiac arrhythmias arise when the pattern of the heartbeat is changed by abnormal impulse initiation or conduction in the myocardial tissue. In general, there are at least two conditions under which the firing of the myocardial cells may become irregular. The first condition is an accessory pathway, which often exists at birth, and may be caused by malformation of the heart. The second condition is usually caused by scare tissue of myocardium that originated from infarction or surgical incisions. Frequently the arrhythmias are due to an arryhthmogenic site which, resulting from one of the above mentioned conditions, does not respond to treatments through the use of anti-arrhythmic drugs. These sites can dominate the normal conduction pathways in the heart resulting in abnormally rapid rhythm or tachycardia which require an interventional remedy.

Currently there are a number of medical and surgical treatments for cardiac arrhythmias. Radio frequency catheter ablation is an interventional technique in which radio frequency energy is delivered, via a catheter, to an electrode in contact with the myocardial tissue. Radio frequency catheter ablation has become a principal form of therapy for paroxysmal supraventricular tachycardia, that is unknown cause of rapid heart rate. Radio frequency catheter ablation is also being used in an increasing number of patients for treatment of ventricular tachycardia (rapid ventricular rate) associated with coronary artery disease and other forms of heart disease. Ventricular tachycardia (VT) is a type of arrhythmia with high morbidity and mortality. RF energy delivery through a standard 7 French, 4 mm distal electrode has been highly successful for ablation of arrythmogenic tissue, i.e. tissue which spontaneously repolarizes, located within a few millimeters of ablation electrodes, such as in patients with accessory atrioventricular (AV) pathways (Wolff-Parkinson-White syndrome) and AV nodal reentrant tachycardia (AVNRT). However, in approximately 1 percent of patients with accessory pathway and in approximately 30 to 50 percent of patients with VT associated with a healed myocardial infraction, the arrhythmogenic tissue, usually located at the epicardial border zone, can be difficult to destroy with a conventional ablation electrode. In order to eliminate the VT foci, deep, transmural lesions, e.g. completely through the myocardium, are necessary for ablation in these patients.

In radio frequency catheter ablation, radio frequency energy causes tissue heating, which, in turn, causes formation of a lesion. With radio frequency ablation, a catheter with a conductive inner core and a metallic tip are placed in contact with the myocardium and a circuit is completed with a patch placed on the patient's body behind the heart. The catheter is coupled to a radiofrequency generator such that application of electrical energy creates localized heating in the biological material and fluids adjacent to the distal emitting electrode. Because of the nature of radiofrequency energy, both the metallic tip and the tissue are heated simultaneously. The peak tissue temperatures during catheter delivered application of RF energy to myocardium occur close to the endocardial surface, such that the lesion size produced is approximately limited by the thermodynamics of radial heat spread from the tip. The amount of heating which occurs is dependent on the amount of contact between the electrode and the tissue and the impedance between the electrode and the exterior surface of the tissue. The higher the impedance, the lower the amount of energy transferred into the tissue.

For any given electrode size and tissue contact area, RF-induced lesion size is a function of RF power level and exposure time, i.e. duration of energy delivery. It has been shown that tissue temperature must exceed 45–50° C. for lethal tissue damage and lesion formation. However, at higher power levels, the application time is frequently limited by a rise in the electrical impedance of the electrode (reducing the application of further heating energy) which can be prevented by maintaining the electrode-tissue interface temperature to less than 100° C. During RF ablation, the tissue heating is related to the difference between the resistive heating and the heat precipitated into the surrounding tissue and blood flow. The ability to destroy tissue is a function of the thermal dose above a threshold value. The thermal dose is approximately equal to the product of temperature and time. In RF tissue ablation, the heat generated at the electrode is based on at least two factors: RF current density and the duration of the RF energy application. The RF current density is approximately equal to the RF current delivered divided by the tissue contact area. The heat dissipated in a local tissue area varies as $1/D^4$ (D sup 4), where D is the distance from the ablation electrode and decreases rapidly as the distance from the ablating electrode increases. The heating is greatest at the surface interface with the electrode, and, if excessive RF power is applied, coagulation, tissue charring and/or rapid impedance rise may occur. For a conventional catheter electrode the limiting factors in creating deeper lesions are the potential risk of coagulation on the electrode, tissue charring and/or rapid impedance rise all as a result of higher electrode-tissue interface temperature when higher power is applied.

Attempts have been made to actively cool the electrode by irrigating or infusing a cooling fluid, such as saline, through the interior lumen of the catheter shaft to an electrode constructed with a degree of porosity to allow the fluid to pass through the electrode and thus cool it. While such cooling may be adequate, temperature control, which is frequently employed, is unusable due to the inhibition of temperature rise of the electrode due to the cooling fluid. As a result excessive energy is often delivered allowing the subsurface temperature to exceed 100° C. which causes steam generation and sub-surface explosions or pops within the myocardial tissue. Moreover, such irrigation procedure can add unnecessary fluid to the patient's circulation that can be potentially hazardous. Additionally, such active cooling mechanisms complicate catheter construction and limit the number of electrodes that may be used. Examples of ablation catheters with electrodes that are actively irrigated during the ablation process are disclosed in U.S. Pat. Nos. 5,545, 161; 5,462,521; 5,437,662; 5,423,811; 5,348,554 and 5,334, 193.

Accordingly a need exists for a simple methodology for permitting greater energy to be delivered to an ablation electrode with minimal risk of overheating the electrode-tissue interface.

A need further exists for a novel catheter electrode design which provides more profound convective electrode cooling, i.e. transferring heat to a surrounding medium, than that of conventional electrode designs.

A further need exists for a catheters employing an electrode design that will allow higher RF power application with longer application duration, resulting in deeper intra-tissue heating and deeper lesions while allowing simpler catheter construction.

A further need exists for an RF ablation catheter in which single or multi-electrode configurations permit the necessary lesion depth to be reached without the risk of overheating.

A further need exists for simple methodology to treat atrial fibrillation by RF catheter ablation using catheter electrodes with small inter-electrode spacing in order to create long linear lesions.

A further need exists for simple methodology to treat focal atrial fibrillation (AF) and atrial flutter that uses a self-cooled electrode to create deeper lesion to eliminate the AF foci and atrial flutter circuit.

SUMMARY OF THE INVENTION

The present invention discloses an ablation catheter which utilizes passive or convective cooling of the electrode(s) to allow deeper lesion formation and to prevent coagulation, tissue charring and/or rapid impedance rise. The self-cooling electrode design has, increased surface area, increased heating capacity, increased thermal mass and periphery on the exterior surface of the electrode which allows for higher current density accumulation and heat transfer at the edges thereof while allowing blood and other biological fluids to flow over the exterior surface of the catheter. The electrode design enables higher rates of power to be delivered to the electrode for greater durations thereby allowing more controlled heating of surrounding tissue while enabling the electrode/tissue junction to remain cooler. A distal tip electrode, according to the invention, may be used on an ablation catheter alone or in conjunction with one or more ring electrodes which may implement some or all of the characteristics of the tip electrode.

According to a first aspect of the invention, electrode for use with catheter comprises an electrode body extending along an axis and having proximal and distal ends; a plurality of channels integrally formed in the electrode body along the exterior surface thereof; a plurality of projections integrally formed in the electrode body along the exterior surface thereof and intermediate the channels, the projections and channels collectively defining a plurality of edges; and means integrally formed in the electrode body for securing the electrode body to the catheter. In some embodiments, the electrode may have a substantially curved exterior surface at the distal end of the electrode body, for use a tip electrode, or a central lumen extending through the electrode body, for use a ring electrode. In another embodiment, the plurality of projections integrally formed within the exterior surface of the electrode extend substantially parallel to the axis of the electrode to form a plurality of axial fins. In another embodiment, the plurality of projections integrally formed within the exterior surface of the electrode extend perpendicular to the axis of the electrode to form a plurality of radial fins. According to an alternate embodiment, the depth of the radial fins decreases in a proximal direction along the exterior surface of the electrode.

According to a second aspect of the invention, an electrode apparatus for use with a catheter comprises an electrode body extending along an axis and having proximal and distal ends; a plurality of channels integrally formed in the electrode body along the exterior surface thereof; a plurality of projections integrally formed in the electrode body along the exterior surface thereof and intermediate the channels, the projections and channels collectively defining a plurality of edges; and means integrally formed in the electrode body for securing the electrode body to the catheter. The projections and channels According to a third aspect of the invention, an electrode apparatus for use with a catheter comprises an electrode body extending along an axis and having proximal and distal ends; a plurality of substantially circular, concave cavities integrally formed within the exterior surface of the electrode body; and means integrally formed in the electrode body for securing the electrode body to the catheter.

According to a fourth aspect of the invention, a method of ablating biological materials comprises: A) providing a catheter having an electrode at a distal region thereof, the electrode having a plurality of channels and projections integrally formed in an alternating pattern on an exterior surface of the electrode, the projections and channels collectively defining a plurality of edges therebetween; B) positioning the electrode so that the exterior surface of the electrode is adjacent the biological material to be ablated; C) supplying energy to the electrode at a rate which causes the electrode to heat; and D) maintaining the position of the electrode so that biological fluids associated with the biological material flow through the channels along the exterior surface of the electrode while heat is simultaneously transferred from the edges and projections to the biological material adjacent the electrode exterior surface.

According to a fifth aspect of the invention, a catheter apparatus comprises an elongate, flexible shaft extending along an axis and having proximal and distal ends; a tip electrode disposed at the distal end of the catheter shaft and having an exterior surface; a first conductor extending through the elongate flexible shaft and electrically coupled to the tip electrode; at least one ring electrode disposed proximal of the tip electrode and having an exterior surface; a second conductor extending through the elongate flexible shaft and electrically coupled to the ring electrode; and a plurality of channels and projections integrally formed in an alternating pattern on the exterior surface of one of the tip electrode and ring electrode, the projections and channels collectively defining a plurality of edges therebetween.

BRIEF DESCRIPTION OF THE DRAWINGS

FIG. 1 illustrates a prior art tip and ring catheter electrode design;

FIGS. 2A–B illustrate side and end views of a tip electrode design with axial surface variations in accordance with the present invention;

FIGS. 3A–B illustrate side and end views of a ring catheter electrode design with axial surface variations in accordance with the present invention;

FIGS. 4A–B illustrate side and end views of a tip electrode design with radial surface variations in accordance with another embodiment of the present invention;

FIGS. 5A–B illustrate side and end views of a ring catheter electrode designs with radial surface variations in accordance with the present invention;

FIGS. 6A–B illustrate perspective views of a tip and ring catheter electrode designs, respectively, both with radial surface variations in accordance with another embodiment of the present invention;

FIGS. 10A–B illustrate an electrode catheter using the electrode designs of FIGS. 6A–B;

FIGS. 12A–B illustrate side cut away views of multi-electrode catheters using the electrode designs of FIGS. 4A–B and 5A–B; and.

FIGS. 13–15 illustrate graphs of experimental data collected using the electrode design of FIG. 8 of the present invention.

DETAILED DESCRIPTION OF THE INVENTION

Figure 7:
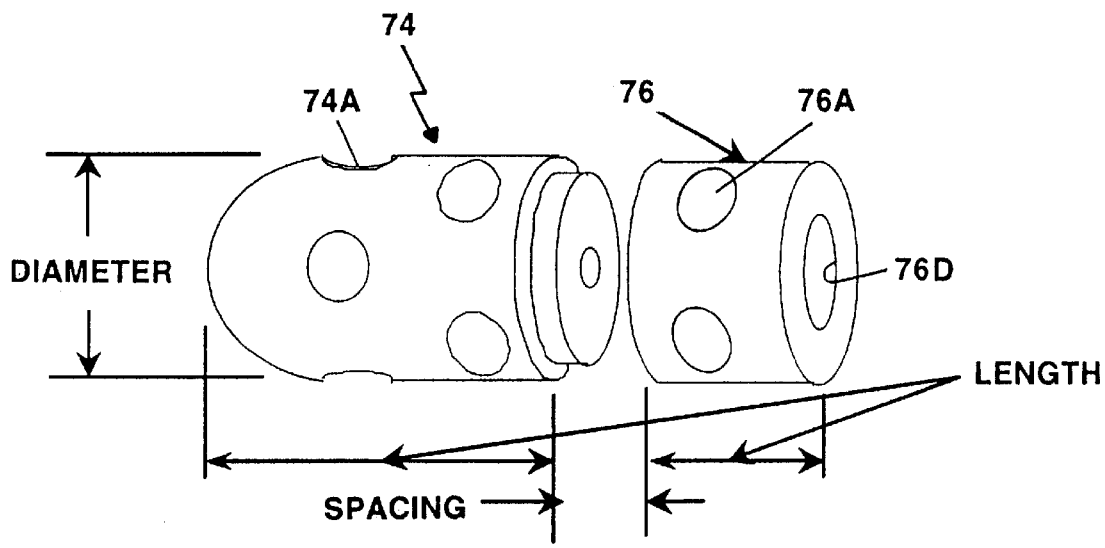
FIG. 7 illustrates perspective views of a tip and ring catheter electrode design, respectively, both with cavity surface variations in accordance with another yet embodiment of the present invention.

The present invention discloses passive, self-cooled electrode designs for use with ablation catheters and other medical devices. FIG. 1 illustrates typical prior art tip and ring electrode designs. As shown, the exterior surface of the electrodes is substantially smooth and the wall thickness is relatively thin in comparison to the diameter of the electrode. In addition the tip electrode is substantially hollow, with a large interior space. Such prior art electrodes heat very quickly and create the problematic conditions described previously during the ablation process.

The present invention provides a self-cooling electrode for use with an ablation catheter. The electrode has greater surface area that allows the electrode to dissipate heat to the blood pool more effectively and has increased thermal mass for greater heating capacity/thermal conductivity for more effective tissue heating. FIGS. 2A–B illustrate a tip electrode 24 according to a first embodiment of the invention. As shown, tip electrode 24 is of a generally solid, cylindrical shape with a curved or rounded distal end. Solid not only refers to the electrode increased wall diameter and mass but also the absence of any lumen or passage which can communicate fluid from an interior cavity in the electrode to the exterior, surface of the electrode. Referring again to the illustrations of FIGS. 2A–B the length of electrode 24 in the illustrative embodiment may be varied according to the intended application while the diameter of the electrode may vary in relation to the diameter of the catheter shaft 12. In the illustrative embodiment, electrode 24 may have the diameter which is the same as, lesser, or greater than the diameter of catheter shaft 12. Some exemplary length and diameter ranges are set forth in Table 1 herein.

Tip electrode 24 may be attached to the distal end of catheter shaft 12 by thermal or adhesive bonding or with a mechanical fastener such as a threaded screw. Alternatively, the proximal end of electrode 24 may be modified to accommodate other techniques of fixing the tip electrode to the catheter shaft. In the illustrative embodiment, tip electrode 24 blocks central lumen 18 from communicating with the area exterior of electrode 24, unlike fluid profusion catheters which allow fluid communication between an interior lumen and the exterior surface of the electrode, electrode 24 is solid.

Electrode 24 may be machine manufactured from any number of biocompatible metals or combinations thereof, including silver, platinum, gold, stainless steel and Nitinol. In addition, an electrode machined from gold and painted with silver may be used with the present invention. Higher thermal characteristics can be obtained with any of the above metals singularly or any alloy to enhance cost versus heat transfer.

In the illustrative embodiment, tip electrode 24 has an increased mass and wall thickness in comparison to prior art electrodes. As illustrated in the various embodiments, the design of the tip electrode varies from employing very thick walls to being solid or nearly solid. Utilizing solid or very thick walls creates an increased cross-sectional area for increased thermal conduction and serves to increase the ability of heat to flow from one region on the surface of the electrode to another. Conventional electrodes, as illustrated in FIG. 1, have very thin walls, typically 0.1 to 0.25 mm or 0.004 to 0.010 inch. By comparison, the electrodes of the present invention have significantly higher internal thermal conductivity, thereby enhancing the transfer of heat from one surface region on the electrode to another. In addition, the increased thermal mass of the inventive electrodes enables longer energy delivery duration in comparison with the conventional electrode designs. Such longer duration allows higher thermal doses to be applied to tissue, resulting in bigger and deeper lesions. Therefore the enhanced convective cooling effect and increased thermal conductivity of the electrode designs disclosed herein allows higher ablation energy levels and longer duration of energy application without the need for irrigation cooling, such as with an irrigated electrode.

The ability to conduct heat from an electrode to the blood flow or to adjacent, cooler regions is related to the electrode surface area. Heat transfer by convection is defined as:

$$q = h \times (\Delta T) \text{ where:} \quad \text{(Equation 1)}$$

ΔT=the temperature difference across the area of interface h=the coefficient of convection heat transfer and h is related to the interface area of the cooling medium with the volume in question for any given medium flow.

Thus, as the electrode/tissue interface surface area increases, convective heat transfer will increase for any temperature difference.

Conductive heat transfer within a solid medium is expressed as:

$$q = k \times (\Delta T / \Delta L) \times A \times \Delta t \text{ where:} \quad \text{(Equation 2)}$$

k=the thermal conductivity of the medium or electrode metal,

ΔT=again the difference in temperature across the path,

ΔL=the length of the conduction path,

A=cross sectional area perpendicular to the heat flow,

Δt=elapsed time.

Therefore, for any metal and temperature difference, as the cross sectional area, proportional to electrode thickness, increases, the quantity of heat transferred through the solid from a higher to a lower temperature also increases. Because of its increased dimensions, electrode 24 has increased thermal mass and thermal conductivity in comparison to prior art electrodes. For the reasons described above, electrode 24 is substantially solid for increased thermal mass, and, therefore, requires a longer time for the energy delivery to reach thermal equilibrium, i.e. targeted ablation temperatures that allow for longer, safe ablation duration.

A plurality of channels 24A extend along the exterior surface of the electrode 24 parallel to the long axis of the electrode to form a plurality of flow paths. Channels 24A enable blood and biological fluids to flow along and over the exterior surface of the electrode 24 further cooling the electrode surface due to the transfer of thermal energy from electrode surface to the surrounding tissue and fluids. Such increased fluid flow helps to maintain a steadier temperature at the electrode/tissue juncture without an active profusion or irrigation system and all of the accompanying negative side effects. In the disclosed embodiment, channels 24A may have a depth of between 3% to 40% of the maximum diameter of the electrode body.

As illustrated, channels 24A further serve to further define a plurality of fin-like projections 24B disposed intermediate the channels 24A. Together channels 24A and projections 24B collectively define a series of edges 24C along the extremities of projections 24B and intermediate the channels 24A. Such design takes advantage of a phenomenon known as the "edge effect" which results in higher concentrations of an electric field, when using RF energy, at surface discontinuities or edges on the electrode surface. This effect causes somewhat higher tissue heating adjacent the surface of the edge features. As such, edges 24C accumulate charge density when RF power is applied thereto and transfer the corresponding increased thermal energy to the surrounding tissue.

Accordingly, a tip electrode 24 having a design similar to FIGS. 2A–B has the following advantages over prior electrode/catheter designs:: i) increased heat capacity which enables a larger amount of heat transfer to the surrounding tissue, ii) increased thermal mass that requires a longer time to reach thermal equilibrium (targeted ablation temperatures), iii) peripheral structures integrally formed on the exterior surface of the electrode to increase the surface area, and thereby, the thermal transfer characteristics of the electrode, iv) a plurality of projections with edges which act as a plurality of charge density accumulation structures and transfer points of greater thermal exchange with the surrounding tissue, and v) a plurality of passages intermediate the projections which enable blood flow across the exterior surface of the electrode thereby further increasing the thermal exchange (cooling) between the electrode and the surrounding tissue and fluids.

FIGS. 4A–B illustrate a tip electrode 44 similar in design to electrode 24 of FIGS. 2A–B except that channels 44A form a series of annular grooves about the exterior surface of electrode 44 in planes which are substantially perpendicular to the long axis of the electrode. As further illustrated in FIGS. 4A–B, a series of radial fin-like projections 44B are disposed intermediate channels 44A. Together channels 44A and projections 44B collectively define a series of edges 44C along the extremities of projections 44B and intermediate and the channels 44A. Otherwise, the theory of operation, dimensions, composition, and techniques for securing electrode 44 to catheter shaft 12 are similar to that described with reference to electrodes 24. The theoretical reasoning for the advantages of the self-cooled design of electrode 44 are also similar to that of electrode 24.

FIG. 6A illustrates a tip electrode 64 similar in design to electrode 44 of FIG. 4A with several differences. Specifically, the distal end of electrode 66 is more bullet-shaped than hemispherical. In addition, channels 64A decrease in diameter more abruptly than channels 44A of electrode 44 creating a series of annular radial projections 64B with edges 66C which have even greater edge effect characteristics. Otherwise, the theory of operation, dimensions, composition, and techniques for securing electrode 64 to catheter shaft 12 are similar to that described with reference to electrodes 24, and 44.

FIG. 7 illustrates a tip electrode 74 similar in design to electrode 14 of FIG. 2A except that channels 44A and projections 44B have been replaced with a plurality of cavities 7 4A integraly formed into the exterior-surface of electrode 74. Specifically, cavity 74A may be generally circular or oval in shape to increase the area of the exterior surface of electrode 74. The depth to which cavities 74A extend below the exterior surface of electrode 74 may be in the range of between 2% to 30% of the maximum diameter of the electrode body. Cavities 74A serve to define a plurality of circular edges at their juncture with the exterior surface of the electrode and provide a space into which blood or other biological fluids may occupy. The cavities 74A increase the effective surface area of electrode 74 and the thermal transfer characteristics of the electrode. Otherwise, the theory of operation, dimensions, composition, and techniques for securing electrode 74 to catheter shaft 12 are similar to that described with reference to electrodes 24 and 44.

Figure 8A:
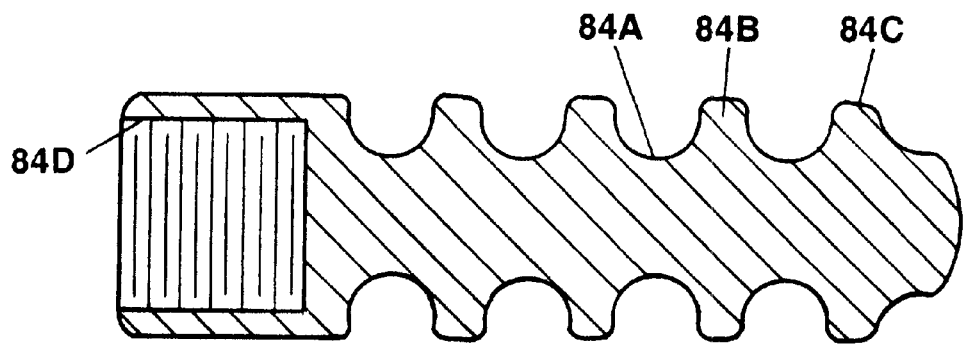
FIGS. 8A–B illustrate side cut-away views of a tip catheter electrode designs with uniform and graduated radial surface variations, respectively, in accordance with another embodiment of the present invention.
Figure 8B:
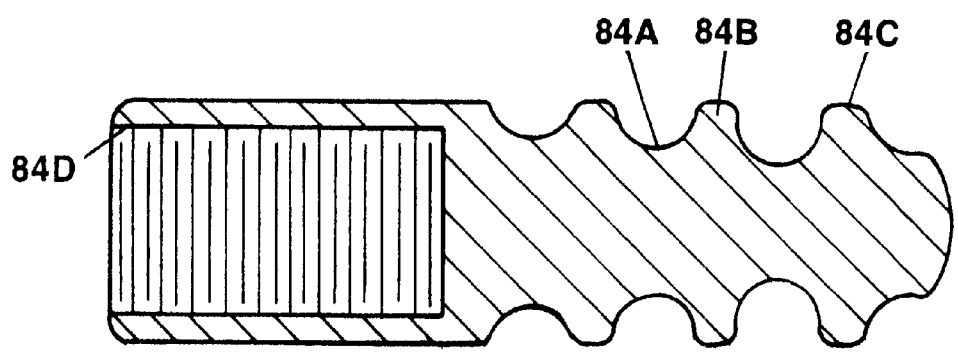

FIGS. 8A–B illustrate related tip electrodes 84 similar in design to electrode 44 of FIGS. 4A–B except that in the embodiment disclosed in FIG. 8B, channels 84A decrease in depth in a proximal direction creating a series of annular radial projections 84B which increase in size in a distal direction. In the embodiment disclosed in FIG. 8A, channels 84A have the same diameter and there are a greater number of projections 84B. In both embodiments, channels 84A and projections 84B collectively define a series of edges 84C along the extremities of projections 84B and intermediate the channels 84A. In addition, electrode 84 includes an optional central cavity 84D which may be threaded to accommodate a complimentary threaded screw disposed in the distal end of catheter shaft 12. The theory of operation, dimensions, composition, and techniques for securing electrode 84 to catheter shaft 12 are similar to that described with reference to electrodes 44 and 64.

Figure 9:
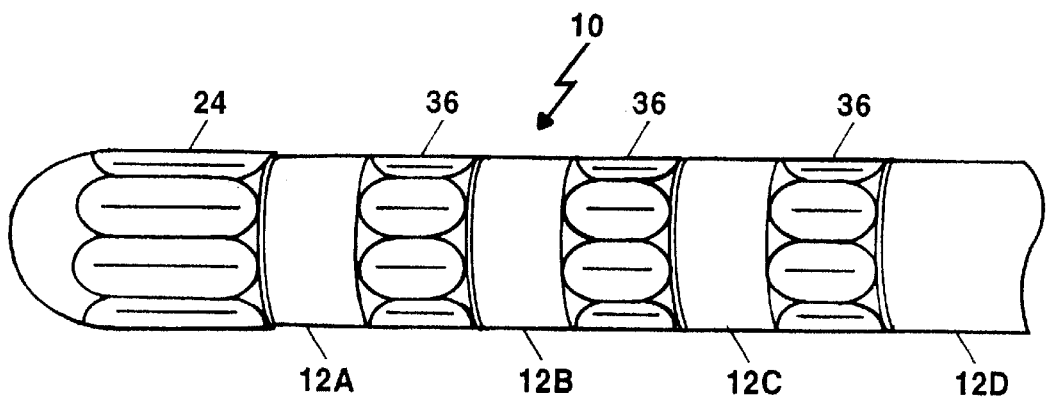
FIG. 9 illustrates a multi-electrode catheter using the electrode designs of FIGS. 2A–B and FIGS. 3A–B.

The tip electrodes described above may be used alone or in conjunction with other electrodes on a catheter, in accordance with the present invention. Specifically, one or more ring electrodes disposed near the distal region of catheter shaft 12 but proximal of the tip electrode may be utilized to create a composite electrode capable of creating deeper, longer lesions during the ablation process. FIGS. 3B, 5B, 6B and 7 illustrate ring electrodes in accordance with the present invention. Ring electrodes 36, 56, 66 and 76 may be attached to catheter shaft 12, about the exterior surface of the catheter shaft, or may be integrally formed within catheter shaft 12 and separated from other electrodes by segments of the shaft body, as illustrated in FIGS. 9–10, as explained hereinafter. Each of ring electrodes 36, 56, 66 and 76 has a central lumen extending therethrough but also has increased wall thickness for increased thermal mass and, therefore, better heat transfer characteristics. As with the distal tip electrode, the ring electrodes may be connected to a power source or monitoring equipment by electrical conductors coupled to the ring electrodes by soldering or other suitable connection means.

Referring to FIGS. 3A–B, a ring electrode 36 includes peripheral structures on the exterior surface thereof which are similar in design to those of electrode 24 of FIGS. 2A–B. Specifically, ring electrode 36 has increased wall thickness and, therefore, increased thermal mass, notwithstanding the central lumen 36D which extends through the electrode body. In addition, a plurality of channels 36A extend longitudinally along the exterior surface of electrode 36 and parallel with the axis of the long electrode. Channels 36A are sized and shaped so as to form a series of fin-like projections 36B intermediate channels 36A. Together channels 36A and projections 36B collectively define a series of edges 36C along the extremities of projections 36B and intermediate and the channels 36A. Each of the projections 36B has a substantially rounded edge which, for the reasons set previously, due to the "edge effect", accumulates charge density when RF power is applied thereto and transfers the corresponding increased thermal energy to the surrounding tissues. Simultaneously, the channels 36A enable blood and biological fluids to flow in between projections 36B for increased cooling of the exterior surface of the electrode 36 by the fluids present at the electrode/tissue juncture, without a need for active profusion or irrigation from within the catheter.

Accordingly, a ring electrode 36 having a design similar to FIGS. 3A–B has the following advantages over prior electrode/catheter designs: i) increased heat capacity which enables a larger amount of heat transfer to the surrounding tissue, ii) increased thermal mass that require a longer time to reach thermal equilibrium (targeted ablation temperatures), iii) peripheral structures integrally formed on the exterior surface of the electrode to increase the surface area, and thereby, the thermal transfer characteristics of the electrode, iv) a plurality of projections with edges which act as a plurality of charge density accumulation structures and transfer points of greater thermal exchange to the surrounding tissue, and v) a plurality of passages intermediate the projections which enable blood flow across the exterior surface of the electrode thereby further increasing the thermal exchange (cooling) between the electrode and the surrounding tissue and fluids.

FIG. 5B illustrates a ring electrode 56 similar in design to electrode 36 of FIG. 3B except that channels 56A form a series of annular grooves about the exterior surface of electrode 56 in series of planes which are substantially perpendicular to the long axis of the electrode 56. As further illustrated in FIG. 5B, a series of radial fin-like projections 56B are disposed intermediate channels 56A. Channels 56A and projections 56B collectively define a series of edges 56C which act as a plurality of transfer points of greater thermal exchange to the surrounding tissue. The theory of operation, dimensions, composition, and techniques for securing electrode 56 to catheter shaft 12 are similar to that described with reference to electrodes 36.

FIG. 6B illustrates a ring electrode 66 similar in design to ring electrode 56 of FIG. 5B, except that channels 66A decrease in diameter more abruptly than channels 56A of electrode 56 thereby creating a series of annular radial projections 66B which have even greater edge effect characteristics. The theory of operation, dimensions, composition, and techniques for securing electrode 66 to catheter shaft 12 are similar to that described with reference to electrodes 36 and 56.

FIG. 7 illustrates a ring electrode 76 similar in design to electrode 36 of FIG. 3B except that channels 36A and projections 36B have been replaced with a plurality of cavities 76A integrally formed into the exterior surface of electrode 76. Specifically, cavity 76A may be substantially circular or oval in shape to increase the area of the exterior surface of electrode 76. The depth to which cavities 76A extend below the exterior surface of electrode 76 may be in the range of between 2% to 30% of the maximum diameter of the ring electrode body. Cavities 76A serve to define a plurality of circular edges at their juncture with the exterior surface of the electrode and provide a space into which blood or other biological fluids may occupy. Otherwise, the theory of operation, dimensions, composition, and techniques for securing electrode 76 to catheter shaft 12 are similar to that described with reference to electrodes 36, 56 and 66.

The number of channels, projections, cavities or any edges formed thereby along the exterior surface of the electrodes, as illustrated in the drawings, should not be construed as limiting. The appropriate number may be determined by the diameter and length of the electrode, the dimensions of the channels and projections and the intended use.

Ablation and diagnostic catheters utilizing the electrodes of the present invention may be implemented as illustrated in any of FIGS. 9–12B. Specifically, a catheter 10 comprises an elongate flexible catheter shaft 12 having proximal and distal extremities. A tip electrode is mounted at the distal extremity of the catheter shaft 12. An electrical conductor extends through the catheter shaft 12 between the tip electrode and a supplying energy, typically radio frequency energy. In addition, catheter 10 may contain one or more ring electrodes disposed along catheter shaft 12 at selected distances from the distal extremity of catheter shaft 12 and proximate tip electrode.

A handle (not shown) may be mounted at the proximal end of catheter shaft 12. The handle may contain multiple ports and be utilized, in the illustrative embodiment, for electrical connections between electrophysiological monitoring equipment and electrical potential sites of the tissue. Electrical conduction means, such as insulated electrically conductive wire, exit through the port for coupling to the electrophysiological monitoring equipment.

Catheter shaft 12 may be manufactured using a known extrusion process from a flexible, durable material, including plastics, such as but not limited to, polyurethanes, polyether-block amides, ionomers, isoplasts, or thermoplastics such as nylon. In an alternative embodiment, an additional kink-resistance braid of a suitable material may be provided within catheter shaft 12 during the extrusion process to reinforce the shaft and to provide additional kink-resistance. The braid (not shown) can be formed of a suitable material such as Nylon or Kevlar and can be provided at the distal region of catheter shaft 12 or any portion of the length of catheter shaft 12, as desired. Catheter shaft 12 may be of varying lengths, the length being determined by the application for catheter 10. Further, catheter shaft 12 may be provided in suitable sizes as, for example, to provide catheters from 3 to 9 French in size. Catheter shaft 12 may include a central lumen 18 extending through shaft 12 for all or part of the shaft length. The diameter of central lumen 18 may be chosen in accordance with the diameter of shaft 12. Alternatively, all or part of catheter shaft 12 may be substantially solid in constitution.

FIGS. 9 and 10A–B disclose ablation catheters which utilize distal tip and ring electrodes in accordance with the present invention to form larger composite electrodes capable of creating deeper, longer lesions during the ablation process. Referring to FIG. 9, a catheter 10 includes a tip electrode 24 affixed to the distal end of catheter shaft 12 and a plurality of ring electrodes 36 spaced at intervals proximal of the tip electrode 24. Tip electrode 24 and ring electrodes 36, as well catheter 10, may be constructed as described herein. Catheter shaft 12 includes a series of short segments 12A–C disposed intermediate ring electrodes 36 and tip electrode 24. As described previously, ring electrodes 36 may be secured intermediate segments of the catheter shaft 12 in a manner similar to that illustrated in FIG. 12A. Referring to FIGS. 10A–B, a catheter 10 includes a tip electrode 64 affixed to the distal end of catheter shaft 12 and a plurality of ring electrodes 66 spaced at intervals proximal of the tip electrode 64. Tip electrode 64 and ring electrode 66, as well catheter 10 may be constructed as described herein. As illustrated in FIG. 10A, catheter 10 comprises a shaft 12 including a series of short segments 12A–C disposed intermediate ring electrodes 66 and tip electrode 64. As described previously, ring electrodes 66 may be secured intermediate segments of the catheter shaft 12 in a manner similar to that illustrated in FIG. 12A. Alternatively, as illustrated in embodiment of FIG. 10B, tip electrode 64 may be secured at the distal end of catheter shaft 12 while electrodes 66 may be disposed about the exterior surface of catheter shaft 12. In such embodiment, electrical conductors extend through the wall of catheter shaft 12 to make electrical contact with ring electrodes 36 in a manner similar to that illustrated in FIG. 12B. Further, in the in embodiment of FIG. 10B one or more of the ring electrodes 66 may be slidably attached to catheter shaft 12 in a manner disclosed in greater detail U.S. Pat. No. 6,178,354, the subject matter of which is incorporated herein by reference.

The catheters illustrated in FIGS. 9–12B are multi-polar catheters useful for creating deep lesions and/or long linear lesions. The spacing between the distal tip electrode and respective ring electrodes in such multi-polar catheters, as well as the diameters and lengths of the electrodes may be as set forth in Table 1 herein.

Figure 11:
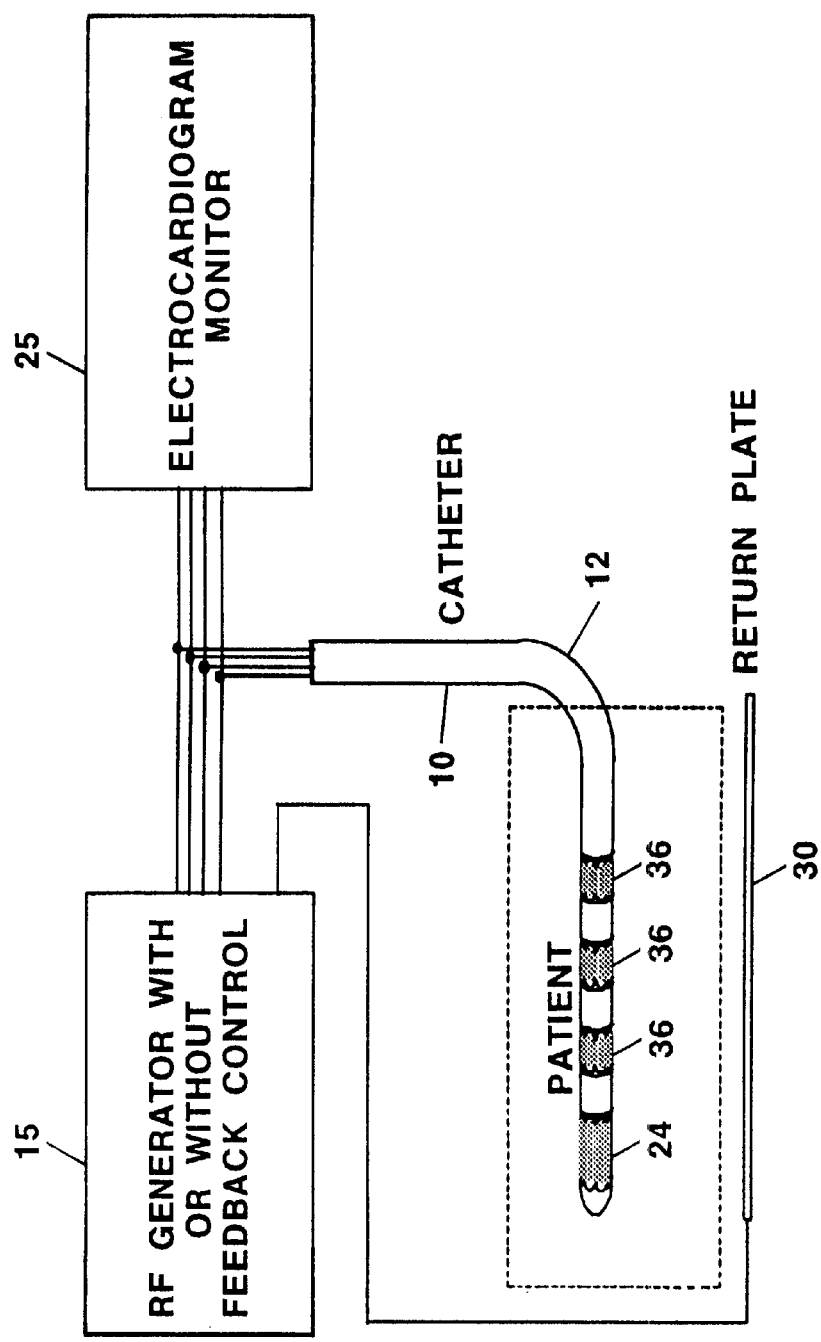
FIG. 11 illustrates conceptually a typical RF ablation system suitable for use with the catheter and electrode designs of the present invention.

FIG. 11 illustrates conceptually a multi-polar catheter 10 as coupled to the other system components during an ablation process. Specifically, catheter 10 is electrically coupled to RF power source 15 and a monitoring device 25, shown here as an electrocardiogram monitor, through conventional electrical connections. Both RF generator 15 and monitoring device 25 may be of a design currently known in the art. Additionally, a return plate 30 is electrically coupled to RF generator 15. In operation, catheter 10 is percutaneously inserted into the patient body and positioned in the vascular system, typically the heart. Once the correct site has been located by the monitoring of the electrophysiological signals of the tissue, ablative energy is delivered to the electrodes. Using the inventive electrodes and catheter described herein, larger and deeper lesions in the cardiac tissue are possible since the self-cooled electrodes remain cooler longer and allow larger amounts of heat to be transferred over an extended time period. Depending on the configuration of RF power source 15 and any additional electrophysiology monitoring equipment, one or more wires may be coupled to each of electrodes 24 and 36. Electrode 24 and any of ring electrodes 36 used in conjunction therewith may be utilized to sense tissue biophysical parameters such as impedance, conductance, admittance, voltage or temperature at, or between, a specified electrode and a return plate (unipolar measurement mode) or between, any multiple specified electrodes (bipolar measurement mode) for use as a control parameter. Further, any of the above-described biophysical parameter signals may be utilized in a feedback control loop, as are know in the arts, to control the amount of power that RF power source 15 provides to the electrodes.

For example, in one embodiment, a thermocouple, thermistor, resistive thermal devices ("RTD"), or the like (not shown), may be coupled to any of electrodes 24 or 36. Such thermo couple device may be disposed in a cavity machined in a portion of the respective electrode body. The temperature sensor has an associated conductive lead (not shown) which extends through the lumen 18 to a signal processor (not shown) for processing the electrical signals generated by the respective temperature sensor. A control system may be included for controlling and regulating the electrical potentials and temperatures in a manner that allows for determination of the ablation effects in the tissue. It is possible to control the distribution of tissue heating by controlling the temperature of tip electrode and the radio frequency voltage, or other energy used, applied between tip electrode and a reference electrode on the surface of the body. The voltage may be set to achieve a desired electrical field strength, and the temperature of tip electrode may be set to provide a desired temperature distribution of the tissue. The temperature distribution will then determine the size of the lesion, i.e., the denatured protein dimensions in the myocardium.

FIGS. 12A–B illustrate side cut away views of multi-electrode catheters 10 using the electrode designs of FIGS. 4A–B and 5A–B. As illustrated in FIG. 12A, catheter 10 comprises a shaft 12 including a series of short segments 12A–B disposed intermediate ring electrodes 56 and tip electrode 44. As described previously, ring electrodes 56 and tip electrode 44 may be secured intermediate segments of the catheter shaft 12 with a suitable bounding agent. Alternatively the electrodes may be mechanically coupled via threads, frictionally snap-fit. An optional steerable wire 19 extends through lumen 18 of shaft 12 and is secured in tip electrode 44 to enable easier placement within the vasculature of the patient. Electrical conductors 21, 23 and 27 extend through lumen 18 and are secured to their respective electrode, typically by soldering or other conventional means.

Alternatively, as illustrated in embodiment of FIG. 12B, tip electrode 44 may be secured at the distal end of catheter shaft 12 while electrodes 56 may be disposed about the exterior surface of catheter shaft 12. In such embodiment, electrical conductors 21 and 23 extend through the wall of catheter shaft 12 to make electrical contact with ring electrodes 56. Although not shown, using electrodes similar to electrodes 84 of FIGS. 8A–B, the tip electrode may be fitted over the distal end of catheter shaft 12 or into distal end of catheter shaft 12.

In treating atrial fibrillation, it is often necessary to create long, linear lesions. This is frequently accomplished by dragging an electrode along a linear path within the atrium requiring longer application time and the potential to loose orientation with the desired line of lesion. Catheters with improved flexibility using short electrodes conforming to the present invention can create a long lesion using more power even in cases of poor contact. Additionally the risk of impedance rise even when simultaneously activating all the electrodes is minimized. Furthermore, because the electrodes of the present invention can be used with higher power, it is possible to use several ring electrodes connected together as a large virtual electrode. Such a technique enables more flexible catheter construction while still having the benefit of a large electrode contact area. Catheters containing the novel electrodes of the present invention can be selected for particular ablation situations by using appropriate effective electrode length and diameter for the site involved. When combined with the special surface structures of these electrodes, improved tissue contact and heating may be obtained. These catheters will simplify the creation of longer, deeper lesions in the biological material.

Table 2 shows statistical results of an experiment using bovine myocardium to compare the time to pop of conventional electrodes versus the electrode 64 disclosed herein. The Specifically, table shows the results and statistical comparison of the time until a pop occurs while delivering 25 watts of RF energy using 8 FR conventional electrode and electrode 64 to bovine myocardium with perpendicular orientation. These tests were conducted in a saline bath with circulating flow at a temperature of 37° C. and the electrode placed on the tissue vertically. On any row in Table 2, "X" marks the results that are compared. With the electrodes described herein, the time until the popping of the subsurface tissue was greatly increased. In Table 2, n represent the number of times the experiment was performed, "endo" refers to endocardium tissue on which the experiment was performed, and "epi" refers to epicardium tissue on which the experiment was performed.

Experimental data in low volume myocardial environments using the self-cooled electrodes disclosed herein, is illustrated in the bar graphs of FIGS. 13–15. In FIG. 13, the lesion depth in mm is graphed. In FIG. 14, the lesion width in mm is graphed. In FIG. 15, the lesion volume cubic mm is graphed. In FIGS. 13–15, column 1 represents lesion data generated using a catheter having a self-cooled electrode, such as electrode 84 of FIG. 8B. Column 2 represents lesion data generated using a catheter having a conventional 8-mm electrode. The data illustrated in the graphs of FIGS. 13–15, is presented as mean±Standard Derivation, with the lower, lighter shaded portion of the bar graphs representing the mean data ands the upper, darker shaded areas of the bar graphs representing the Standard Derivation. The experiment was conducted with a custom-made in vitro apparatus with fresh bovine heart ventricular tissue submerged in the temperature-controlled blood bath at 37° C.

As illustrated, even in a low volume environment, the self-cooled electrodes described herein perform significantly better with less incident of tissue charring or popping than conventional ablation electrode/catheter designs. This set of preliminary experimental data was collected at 0.5 liter/minute flow rate. (In physiologically relevant condition, flow rate ranging from 1–3 liter/minutes. Even at this physiologically very low flow rate the catheters with self-cool electrode demonstrated the ability to create bigger and deeper lesion.

It is conceivable and demonstrated that the improved performance of the inventive self-cooled electrodes will be amplified by increasing of flow rate, since the cooling effect of the electrode design will be more profound with greater blood flow across the electrode surface. From the preliminary experimental data, at high flow rate with higher RF energy, 9–12 mm deep lesions were created using this self-cooled electrode design.

Although the inventive passively cooled electrodes disclosed herein have been described with reference to RF ablation techniques it will be obvious to those skilled in the arts that other sources of electromagnetic energy, such as microwave, ultrasound, and laser energy may be coupled to the tip and ring electrodes of the invention. Further, although the invention has been described with reference to the heart and myocardial tissue, procedures involving other biological material and fluid benefit similarly. The invention can be employed with any procedure using energy induced tissue heating, the increased convective cooling being applicable to other heating technologies to minimize tissue-electrode interface overheating.

TABLE 1

Possible electrode configurations and uses
Self-cooled electrode dimensions and configurations

| DIAMETER | LENGTH | SPACING | USED FOR |
|---|---|---|---|
| 6 FR | 4 mm, 6 mm | 1.5 mm, 2 mm | Long linear |
|  | 8 mm, 10 mm | 3 mm, 4 mm | lesions |
| 7 FR | 4 mm, 6 mm | 1.5 mm, 2 mm | Long/deep |
|  | 8 mm, 10 mm | 3 mm, 4 mm | lesions |
| 8 FR | 4 mm, 6 mm | 1.5 mm, 2 mm | Longer/deep |
|  | 8 mm, 10 mm | 3 mm, 4 mm | lesions |

TABLE 2

|  | Conventional electrode | | | Self-cooled electrode of this Invention | | |
|---|---|---|---|---|---|---|
| All points | Endo n = 7 | Epi n = 9 | Combined n = 16 | endo n = 5 | epi n = 9 | combined n = 14 |
| Mean (seconds)→ | 15.6 ± 6.5 | 16.7 ± 6.8 | 15.3 ± 7 | 21.1 ± 11.8 | 27.3 ± 9.2 | 24.6 ± 10.5 |
| p 0.160 | X | | | X | | |
| p 0.0068 | | X | | | X | |
| p 0.0038 | | | X | | | X |
| 1 outlier removed | | | n = 15 | | | n = 13 |
| Mean (seconds)→ | | | 14.4 ± 6.4 | | | 25.9 ± 9.6 |
| p 0.0004 | | | X | | | X |

What is claimed is:

1. A catheter apparatus comprising:
   a shaft extending along an axis and having proximal and distal ends;
   an electrode disposed near the distal end of the shaft and having an exterior surface;
   the electrode has a central lumen extending therethrough to form an annular ring electrode disposed proximal of the distal end of the shaft;
   a plurality of channels integrally formed in the electrode along the exterior surface thereof;
   a plurality of projections integrally formed in the electrode along the exterior surface thereof and intermediate the channels, the projections and channels collectively defining a plurality of edges; and a conductor extending through the shaft and electrically coupled to the electrode.

2. The apparatus of claim 1 wherein the plurality of projections integrally formed along the exterior surface of the electrode extend substantially parallel with the axis of the shaft.

3. The apparatus of claim 1 wherein the plurality of projections integrally formed along the exterior surface of the electrode extend substantially perpendicular to the axis of the shaft.

4. The apparatus of claim 1 wherein the electrode is movable relative to the shaft.

5. An electrode apparatus for use with a catheter comprising:
- an electrode body extending along an axis and having proximal and distal ends and an exterior surface;
- a central lumen extending through the electrode body;
- a plurality of channels integrally formed in the electrode body along the exterior surface thereof; and
- a plurality of projections integrally formed in the electrode body along the exterior surface thereof and intermediate the channels, the projections and channels collectively defining a plurality of edges.

6. The apparatus of claim 5 wherein the plurality of projections integrally formed along the exterior surface of the electrode extend substantially parallel with the axis of the electrode.

7. The apparatus of claim 5 wherein the plurality of projections integrally formed along the exterior surface of the electrode extend substantially perpendicular to the axis of the electrode.

8. An electrode apparatus for use with a catheter comprising:
- an electrode body extending along an axis and having proximal and distal ends and an exterior surface;
- a central lumen extending through the electrode body;
- a plurality of channels integrally formed in the electrode body along the exterior surface thereof and substantially parallel with the axis of the electrode body; and
- a plurality of projections integrally formed in the electrode body along the exterior surface thereof and intermediate the channels, the plurality of projections extending substantially parallel with the axis of the electrode body, the projections and channels collectively defining a plurality of edges.

9. An electrode apparatus for use with a catheter comprising:
- an electrode body extending along an axis and having proximal and distal ends and an exterior surface;
- a central lumen extending through the electrode body;
- a plurality of channels integrally formed in the electrode body along the exterior surface thereof and substantially perpendicular to the axis of the electrode body; and
- a plurality of projections integrally formed in the electrode body along the exterior surface thereof and intermediate the channels, the plurality of projections extending substantially perpendicular to the axis of the electrode body, the projections and channels collectively defining a plurality of edges.

10. An electrode apparatus for use with a catheter comprising:
- an electrode body extending along an axis and having proximal and distal ends and an exterior surface;
- a central lumen extending through the electrode body;
- a plurality of substantially circular, concave cavities integrally formed along the exterior surface of the electrode body; and
- means integrally formed in the electrode body for securing the electrode body to the catheter.

11. A method of ablating biological materials comprising:
A) providing a catheter having an electrode at a distal region thereof, the electrode having an electrode body and a central lumen extending through the electrode body; the electrode having a plurality of channels and projections integrally formed in an alternating pattern on an exterior surface of the electrode, the projections and channels collectively defining a plurality of edges therebetween;
B) positioning the electrode so that the exterior surface of the electrode is adjacent the biological material to be ablated;
C) supplying energy to the electrode at a rate which causes the electrode to heat;
D) maintaining the position of the electrode so that biological fluids associated with the biological material flow through the channels along the exterior surface of the electrode while heat is simultaneously transferred from the edges and projections to the biological material adjacent the electrode exterior surface.

12. A catheter apparatus comprising:
- an elongate, flexible shaft extending along an axis and having proximal and distal ends;
- a tip electrode disposed at the distal end of the elongate flexible shaft and having an exterior surface;
- a first conductor extending through the elongate flexible shaft and electrically coupled to the tip electrode;
- at least one ring electrode disposed proximal of the tip electrode and having an exterior surface;
- a second conductor extending through the elongate flexible shaft and electrically coupled to the ring electrode; and
- a plurality of channels and projections integrally formed in an alternating pattern on the exterior surface of the ring electrode, the projections and channels collectively defining a plurality of edges therebetween.

13. The apparatus of claim 12 wherein the plurality of channels and projections integrally formed along the exterior surface of the ring electrode extend substantially parallel with the axis of the elongate, flexible shaft.

14. The apparatus of claim 12 wherein the plurality of channels and projections integrally formed along the exterior surface of the ring electrode extend substantially perpendicular to the axis of the elongate, flexible shaft.

15. The apparatus of claim 12 wherein the ring electrode is movable relative to the elongate flexible shaft.

16. An electrode for use with a catheter and a source of electromagnetic energy comprising:
- an electrode body extending along an axis and having proximal and distal ends, the electrode body further having a central lumen extending therethrough and an exterior surface with a substantially smooth portion;
- a plurality of channels integrally formed in the electrode body along the exterior surface thereof; and
- a plurality of projections integrally formed in the electrode body along the exterior surface thereof and intermediate the channels, the projections and channels collectively defining a plurality of edges along the exterior surface of the electrode body,
- the edges capable of accumulating higher concentrations of electrical charge than the smooth portion of the exterior surface, when electromagnetic energy is received from the source.

17. An electrode for use with a catheter and a source of electromagnetic energy comprising:

an electrode body extending along an axis and having proximal and distal ends, the electrode body having a central lumen extending therethrough and an exterior surface with a substantially smooth portion;

a plurality of channels integrally formed in the electrode body along the exterior surface thereof; and a plurality of projections integrally formed in the electrode body along the exterior surface thereof and intermediate the channels, the projections and channels collectively defining a plurality of edges along the exterior surface of the electrode body, the edges capable of transferring greater thermal energy to adjacent biological material than the smooth portion of the exterior surface, when electromagnetic energy is received from the source.

18. A catheter apparatus comprising:

an elongate, flexible shaft extending along an axis and having proximal and distal ends;

a tip electrode disposed at the distal end of the elongate flexible shaft and having an exterior surface;

a first conductor extending through the elongate flexible shaft and electrically coupled to the tip electrode;

at least one ring electrode disposed proximal of the tip electrode and having an exterior surface;

a second conductor extending through the elongate flexible shaft and electrically coupled to the ring electrode; and a plurality of substantially circular, concave cavities integrally formed within the exterior surface of the ring electrode.

19. The apparatus of claim 18 wherein the ring electrode is movable relative to the elongate flexible shaft.

* * * * *